United States Patent [19]

Studt et al.

[11] Patent Number: 4,742,055
[45] Date of Patent: * May 3, 1988

[54] 3- AND 5-AMINO THIATRIAZINES, AND THEIR PHARMACEUTICAL USES

[75] Inventors: William L. Studt, Harleysville; Donald E. Kuhla, Doylestown; Henry F. Campbell, Lansdale; Stuart A. Dodson, Lansdale, all of Pa.

[73] Assignee: Rorer Pharmaceutical Corporation, Fort Washington, Pa.

[*] Notice: The portion of the term of this patent subsequent to Jun. 17, 2003 has been disclaimed.

[21] Appl. No.: 604,988

[22] Filed: Apr. 27, 1984

[51] Int. Cl.$^4$ ............... C07D 285/00; C07D 401/12; C07D 417/12; A61K 31/54
[52] U.S. Cl. .................... 514/222.5; 544/7; 544/2; 544/3; 544/5; 540/481; 540/467; 540/544; 540/598
[58] Field of Search .............. 544/7, 2, 3, 5; 424/246; 260/243.3; 514/222; 540/598, 544, 481, 467

[56] References Cited

U.S. PATENT DOCUMENTS

| | | | |
|---|---|---|---|
| 2,454,261 | 11/1948 | Walter | 544/7 |
| 4,316,015 | 2/1982 | Hamprecht et al. | 544/7 |
| 4,343,648 | 8/1982 | Hamprecht et al. | 544/7 |
| 4,426,219 | 1/1984 | Hamprecht et al. | 544/7 |
| 4,472,191 | 9/1984 | Hamprecht et al. | 544/7 |
| 4,497,810 | 2/1985 | Hoffman | 544/7 |
| 4,595,683 | 6/1986 | Kuhla et al. | 514/222 |

FOREIGN PATENT DOCUMENTS 104611 4/1984 European Pat. Off. .

Primary Examiner—John M. Ford
Attorney, Agent, or Firm—James A. Nicholson; Alexis Barron; Martin F. Savitzky

[57] ABSTRACT

A class of 3- and 5-amino thiatriazine compounds exhibiting pharmacological activity, including anti-ulcerogenic and gastrointestinal cytoprotective activity, pharmaceutical compositions comprising these compounds, and methods for the treatment of gastrointestinal hyperacidity and ulcerogenic disorders in mammals using said compositions.

19 Claims, No Drawings

3- AND 5-AMINO THIATRIAZINES, AND THEIR PHARMACEUTICAL USES

FIELD OF THE INVENTION

This invention relates to a class of thiatriazine compounds characterized by an amino substituent in the 3- and/or the 5-position of the thiatriazine ring and methods for the treatment of physiological disorders, including gastrointestinal disorders in humans and other mammals.

REPORTED DEVELOPMENTS

Gastrointestinal hyperacid secretion, stomach and intestinal ulceration, and gastritis are major gastrointestinal disorders observed in the general adult populations of industrialized societies. Many factors, including the production of excess gastric acid and the weakening of the lining of the stomach and gastrointestinal tract against such acid are implicated as causes of these disorders. Traditional treatment of these disorders has involved the administration of antacids to neutralize the excess gastric acid and the administration of antisecretory drugs which generally reduce the production of all gastric secretions.

In the last few years, the treatment of gastrointestinal disorders such as peptic ulcer has changed to include the use of anti-secretory drugs which selectively block the production of gastric acid. These drugs are believed to interfere with the body's physiological pathway responsible for the production of gastric acid by blocking the action of histamine. Histamine production is induced in the body by a number of stimuli, including stress, allergic reaction, etc., and acts to increase gastric secretion, dilate blood vessels and stimulate smooth muscle tissue. Histamine is believed to function by way of interaction with histamine receptors in the body. The subdivision of these receptors into two groups, the $H_1$- and $H_2$-receptors, was proposed by Ash and Schild (Brit. J. Pharmacol. Chemother, 1966, 27, 427) and Black et al (Nature 1972, 236, 385). The $H_1$-receptor is involved in the bronchial and gastrointestinal smooth muscle stimulative action of histamine. Drugs which block this action are labelled "antihistamines" (e.g. mepyramine).

Black et al, cited above, described the group of substances which act at histamine receptors other than the $H_1$-receptor as the $H_2$-receptors. Blocking the action of histamine at the $H_2$-receptors will selectively block histamine's stimulative action on gastric acid secretion and heart rate. Burimamide was the first clinically effective $H_2$-receptor antagonist inhibiting gastric secretion in man; but Burimamide's oral absorptivity is poor. Subsequent studies developed the orally active Metiamide, the side effects of which limited clinical use, and Cimetidine which has been marketed as an anti-ulcer drug. A number of classes of heterocyclic chemical compounds have been reported as $H_2$-receptor antagonists, for example, those disclosed in U.S. Pat. Nos. 4,104,381, 4,279,819, 4,323,566, 4,390,701, 4,395,553, and British published patent applications GB No. 2067987A and GB No. 2047238A, and EPO No. publication 0081955A2, the disclosures of which are incorporated by reference.

Another method for the prevention or treatment of gastric ulcer comprises the use of drugs which neither neutralize nor inhibit the secretion of gastric acid. These drugs constitute a class of anti-ulcer compounds which function to enhance the normal defense mechanisms of the body, rather than to reduce normal body secretions, and are described as "cytoprotective" agents. It has been proposed that such agents act to strengthen the mucosal lining of the gastrointestinal system by one or more mechanisms, thereby preventing any damage which could result from the action of strong gastric acid. Prostaglandins have been implicated in the mechanism of cytoprotection by a number of workers in the field. See, the discussion of cytoprotection in Robert, Andre, "Prostaglandins and Digestive Diseases", *Advances in Prostaglandin and Thromboxane Research*, Vol. 8 (Raven Press, N.Y. 1980), and Robert et al, "Cytoprotection by Prostaglandins in Rats", *Gastroenterology*, 77, 433–443 (1979), hereby incorporated by reference. Drugs, other than prostaglandins, which exhibit cytoprotective activity include carbenoxolone sodium, reported to exhibit undesirable side effects, such as edema, diastolic hypertension or hypokalemia, and the thiazol-2-yl- carbamoylcarboxylic acids, esters and imides described in U.S. Pat. No. 4,321,372.

Thiatriazines are disclosed for use as herbicides, fungicides, and/or bacteriocides in U.S. Pat. Nos. 3,817,993; 4,007,175; 3,915,688; 4,013,447; 4,316,015; 4,343,648; 4,425,152 and 4,426,219; EPO Appl. Ser. Nos. EP 0073443A1 and EP 0071051A1; Ger. Pat. Nos. DE 3,013,268; DE 3,143,381; DE 3,134,145; Ger. Offen. No. 2,337,867; Ger. Offen. 2,933,889; E. Ger. No. 142,338; and No. 113,006.

Compounds of the present invention comprise amino thiatriazines which exhibit pharmaceutical activity in humans such as gastrointestinal activity including anti-ulcer activity and cytoprotective activity.

SUMMARY OF THE INVENTION

The present invention relates to a method for the therapeutic treatment of a human or other mammal comprising administering thereto a therapeutically effective amount of a 1,2,4,6-thiatriazine-1,1-dioxide compound substituted in the 3- and/or the 5-position by an amine substituent.

Another aspect of this invention relates to a class of compounds, effective in the treatment of gastrointestinal disorders in mammals, of Formula I

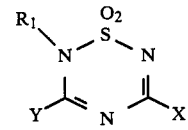

wherein:
$R_1$ is H, alkyl, cycloalkyl, aralkyl or heterocyclylalkyl;
X and Y are each independently halo, hydroxy, alkyl, aryl, alkoxy, mercaptyl, alkylmercaptyl, alkoxyalkyl, hydroxyalkyl, aralkyl, aryloxyalkyl, and amine; provided that at least one of X or Y is an amine substituent and further provided that when X is an amine, then Y is other than halo or hydroxy;
or a pharmaceutically acceptable salt thereof.

Compounds within the scope of Formula I exhibit physiological activity in mammals including anti-secretory activity, histamine $H_2$-receptor antagonist activity, anti-ulcer activity and cytoprotective activity.

DETAILED DESCRIPTION OF THE INVENTION

A preferred class of compounds according to this invention is described by Formula II:

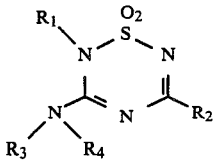

wherein
$R_1$ is H, alkyl, cycloalkyl, aralkyl or heterocyclalkyl;
$R_2$ is $NR_5R_6$, alkyl, aryl, aralkyl, alkoxy, aryloxy, aryloxyalkyl, hydroxyalkyl, alkoxyalkyl, halo, hydroxy, mercapto or alkylmercapto;
$R_3$ is H or alkyl;
$R_4$ is H, alkyl, aryl, aralkyl, aryloxyalkyl or $-(CH_2)_m-Z-(CH_2)_n-B$;
$R_5$ and $R_6$ are each independently H, alkyl, aryl, alkanoyl, carbamoyl, alkylcarbamoyl, amidino, or $-(CH_2)_m-Z-(CH_2)_n-B$;
Z is oxygen or sulfur;
m and n are 0, 1, 2, 3 or 4, provided
$m+n \neq 0$; and
B is aryl, heteroaryl, alkylheteroaryl, bicyclic aryl, bicyclic heteroaryl, alkyl bicyclicheteroaryl, bicyclic tetrahydroaryl, bicyclic heterotetrahydroaryl or alkyl bicyclic heterotetrahydroaryl, and aryl, heteroaryl, bicyclic aryl, bicyclicheteroaryl, bicyclic tetrahydroaryl and bicyclic heterotetrahydroaryl substituted by amino, aminoalkyl, alkylamino, dialkylamino, alkylaminoalkyl, dialkylaminoalkyl, or azaheterocyclyl; or
a pharmaceutically acceptable salt thereof.

A most preferred class of compounds according to Formula II comprises compounds wherein:
$R_1$ is H, alkyl, cycloalkyl or aralkyl;
$R_2$ is amino, alkylamino, dialkylamino, or alkoxy;
$R_3$ is hydrogen; and
$R_4$ is $-(CH_2)_m-Z-(CH_2)_n-B$.

A particularly preferred class of B substituent groups according to Formula II is selected from the following:

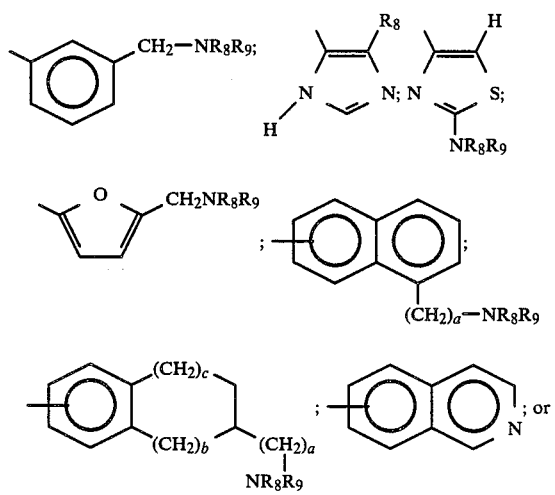

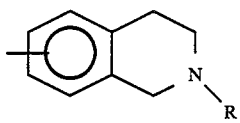

wherein:
a is 0, 1 or 2;
b is 0 or 1;
c is 0, 1, 2 or 3;
R is H, lower alkyl or arloweralkyl;
$R_8$ and $R_9$ together are lower alkylene and together with the nitrogen atom to which they are attached form a heterocycle which may include one or more additional heteroatoms of N, O or S.

A special embodiment of compounds according to Formula II comprises the class wherein:
$R_1$ is H, lower alkyl, cycloloweralkyl or phenylloweralkyl;
$R_2$ is $NH_2$;
$R_3$ is H or lower alkyl; and
$R_4$ is a bicyclic benzenoid alkylene ether group of the formula

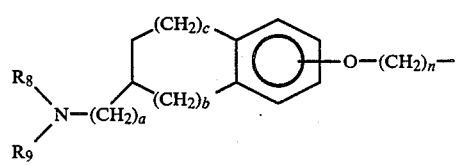

wherein:
a, b and c are 0, 1 or 2;
n is 2, 3 or 4;
$R_8$ and $R_9$ are each independently H or loweralkyl; or
$R_8$ and $R_9$ together with the nitrogen to which they are attached form a hetero ring which may contain one or two additional hetero atoms of N, O or S.

A particularly preferred subclass of this embodiment is described by:
a is 0 or 1;
b is 0;
c is 1 or 2;
n is 3 or 4;
$R_1$ is lower alkyl;
$R_3$ is H; and
$NR_8R_9$ is 1-piperidinyl, 1-pyrrolidinyl or 1-morpholinyl.

The compounds of Formula I may also form hydrates and exhibit tautomerism. Formula I is intended to encompass all hydrates and tautomers, as well as any diastereomers and optical enantiomers.

As employed above and throughout the disclosure, the following terms, unless otherwise indicated, shall be understood to have the following meanings:

"Alkyl" means an aliphatic group. "Lower alkyl" is an alkyl group having 1 to about 4 carbon atoms and is preferred. Examples of lower alkyl groups are methyl, ethyl, n-propyl, isopropyl, butyl, sec-butyl, and tert-butyl.

"Cycloalkyl" means a cyclic aliphatic group. "Cycloloweralkyl" is a group having about 3 to about 7 carbon atoms and is preferred.

"Heterocyclic ring" means a nitrogen-containing ring of the formula

where Y is alkylene or alkylidinyl having from one to six carbon atoms, and may include one to three atoms of N, O or S. Exemplary heterocyclic groups include piperidinyl, pyrrolidinyl, morpholinyl, azepinyl, pyrrolyl, imidazolyl, pyrazolyl, and thiamorpholinyl.

"Heteroaryl" means a five or six membered monocyclic ring or 9 or 10 membered bicyclic ring either of which may contain one or more heteroatoms of nitrogen, oxygen or sulfur, including furyl, pyridyl, thiazolyl, quinolinyl, indolyl or thienyl.

"Aryl" means an aromatic hydrocarbon radical group such as phenyl, toluyl, and includes phenyl or toluyl substituted by one or more substituent groups including lower alkyl, halo, carboxyl, amino, loweralkyl amino, amido, hydroxyl, nitro, cyano, or sulfonyl. Preferred aryl groups include phenyl and toluyl.

"Bicyclic aryl or bicyclic heteroaryl" means a fused bicyclic radical group such as naphthyl, indanyl, quinolinyl or isoquinolinyl.

"Bicyclic tetrahydroaryl or bicyclic tetrahydroheteroaryl" means a fused reduced bicyclic radical group such as tetrahydronaphthyl, tetrahydroquinolinyl or tetrahydroisoquinolinyl.

"Amine substituent" means a radical group of the formula

wherein $R_3$ and $R_4$ are as defined above.

Compounds of this invention may be prepared according to the exemplary means described below and by analagous means known to those skilled in the art.

The preparation of the B radical is fully described in U.S. Pat. Nos. 4,104,381; 4,279,819; 4,323,566; 4,390,701; 4,395,553; and GB No. 2047238A; GB No. 2067987A, and EPO publication No. 0081955A2; and copending U.S. application Ser. Nos. 489,702 and 489,814 (both assigned to the assignee of the present application) and International application Ser. No. PCT/84/00657 and U.S. Ser. No. 604,813, filed concurrently herewith, all of which are hereby incorporated by reference.

The following are selected examples of the preparation of compounds according to this invention which utilize starting materials which are either commercially available, prepared according to methods known in the art or described in the above references, incorporated by reference.

EXAMPLE 1

3-Amino-2-n-BUTYL-5-ETHOXY-2H-1,2,4,6-THIA-TRIAZINE-1,1-DIOXIDE

Ammonia gas is bubbled into a stirred solution of 2-n-butyl-5-ethoxy-3-p-nitrophenoxy-2H-1,2,4,6-thiatriazine-1,1-dioxide (9.2 g) in methylene chloride(125 ml) cooled in a methanolic ice bath for about 25 min. The reaction mixture is allowed to warm to RT and excess ammonia evaporated. The reaction mixture is partitioned between 5% aqueous NaOH and methylene chloride and the aqueous layer separated and acidified to about pH 9. The precipitate is filtered and the filtrate extracted with methylene chloride. The dried (MgSO₄) methylene chloride extract is evaporated and the solids are combined and recrystallized from hot toluene yielding the desired 3-amino product as a solid, M.P. 152–153° C.

EXAMPLE 2

2-n-Butyl-5-METHOXY-3-[3-[5-[1-(1-PIPERIDINYL)-1,2,3,4-TETRAHYDRONAPH-THYLOXY]]-PROPYLAMINO]-2H-1,2,4,6-THIA-TRIAZINE-1,1-DIOXIDE Step 1. 2-n-Butyl-5-methoxy-3-p-nitrophenoxy-2H-1,2,4,6-thiatriazine-1,1-dioxide A solution of 2-n-butyl-3-chloro-5-methoxy-2H-1,2,4,6-thiatriazine-1.1-dioxide (38 g) in methylene chloride (250 ml) is added dropwise to a stirred mixture of p-nitrophenol (28 g) and triethylamine (41 g) in methylene chloride (230 ml). The reaction mixture is refluxed for about 3.5 hours, cooled and partitioned between saturated aqueous Na₂CO₃ and methylene chloride. The methylene chloride layer is separated, washed, dried and concentrated. The residue is dissolved in isopropyl acetate, treated with charcoal, filtered and the filtrate concentrated and cooled. The precipitate is filtered and the filtrate concentrated to an oil which is chromatographed on silica gel using methylene chloride as eluent. The pure fractions are combined, concentrated and crystallized from ether yielding the desired p-nitrophenoxy product as a solid, M.P. =52–55° C.

Step 2. 2-n-Butyl-5-methoxy-3-[3-[5-[1-(1-piperidinyl)-1,2,3,4-tetrahydronaphthyloxy]]-propylamino]-2H-1,2,4,6-thiatriazine-1,1-dioxide A solution of the p-nitrophenoxy compound from Step 1 above in methylene chloride (60 ml) is added dropwise to a stirred mixture of 3-[5-[1-(1-piperidinyl)-1,2,3,4-tetrahydronaphthyloxy]]propylamine (8.7 g) and triethylamine (4 g) in methylene chloride (90 ml). The reaction mixture is stirred at RT for 4 hours and extracted with aqueous saturated Na₂CO₃. The methylene chloride fraction is dried over MgSO₄, filtered and concentrated yielding the desired product as an oil.

EXAMPLE 3

5-AMINO-2-n-BUTYL-3-[3-[5-[1-(1-PIPERIDINYL)-1,2,3,4-TETRAHYDRONAPHTHYLOXY]]-propylamino]-2H-1,2,4,6-thiatriazine Liquid ammonia (15–20 ml) is added to a solution of the 2-n-butyl-5-methoxy compound of Example 2 above (19 g) in methanol (80 ml) stirred in a bomb cooled in a dry ice/acetone bath. The bomb is sealed and heated at 60°–90° C. for about two days. The reaction mixture is cooled and concentrated in vacuo and the residue chromatographed on silica gel (300 g) (eluent=CH₂Cl₂ and 1% MeOH/CH₂Cl₂). The fractions (the slowest eluted with 1% MeOH/CH₂Cl₂) are combined, concentrated in vacuo and dissolved in methanol. Methanesulfonic acid (1.4 g) is added to the solution and the solution evaporated in vacuo forming a white foam which is dissolved in water. The aqueous solution is washed with ethyl acetate, basified to pH 9–10 and extracted with methylene chloride. The organic extract is dried, filtered and the solvent evaporated to yield the desired product as a foam, M.P. =70–80° C.

EXAMPLE 4

2-n-Butyl-3-[(2-(2-GUANIDINO)THIAZOL-4-YLMETHYLTHIO)ETHYLAMINO]-5-METHOXY-2H-1,2,4,6-THIATRIAZINE-1,1-DIOXIDE A solution of 2-n-butyl-5-methoxy-3-p-nitrophenoxy-2H-1,2,4,6-thiatriazine (10.7 g) in methylene chloride (50 ml) is added dropwise to a stirred mixture of 2-[(2-guanidino)thiazole-4-ylmethylthio]ethylamine (9.1 g), triethylamine (13 g) in methylene chloride (80 ml) and the mixture stirred at RT for about 18 hours. The reaction mixture is partitioned between saturated aqueous $Na_2CO_3$ and methylene chloride. The organic layer is separated, dried over $MgSO_4$, filtered, and the filtrate concentrated in vacuo. The residue is taken up in methylene chloride, washed with 1N NaOH solution, dried over $MgSO_4$, filtered and concentrated to give the desired product as a foam.

EXAMPLE 5

5-AMINO-2-n-Butyl-3-[(2-(2-GUANIDINO)-THIAZOL-4-YLMETHYLTHIO)AMINO]-2H-1,2,4,6-thiatriazine-1,1-dioxide A mixture of 2-n-butyl-3-[(2-(2-guanidino)thiazol-4-ylmethylthio)ethylamino]-5-methoxy-2H-1,2,4,6-thiatriazine-1,1-dioxide (13 g), and liquid ammonia (10 ml) in methanol (70 ml) is heated to 90° C. in a bomb for about 72 hours. The reaction mixture is cooled, concentrated in vacuo and the residue chromatographed on silica gel (240 g) eluting with 10% $MeOH/CH_2Cl_2$. The major fractions are concentrated yielding a foam/oil which is triturated with ether forming a solid which is filtered and dried in a vacuum dessicator yielding the desired product.

The free base and a molar amount of maleic acid are dissolved in acetone forming the maleate salt which is recrystallized from hot isopropyl alcohol and dried in vacuo, M.P.=149-151° C.

EXAMPLE 6

3-AMINO-5-METHOXY-2-METHYL-2H-1,2,4,6-THIATRIAZINE-1,1-dioxide

Step 1. 5-Methoxy-2-methyl-3-p-nitrophenoxy-2H-1,2,4,6-thiatriazine-1,1-dioxide

A solution of 3-chloro-5-methoxy-2-methyl-2H-1,2,4,6-thiatriazine-1,1-dioxide (48 g) in methylene chloride (25.5 ml) is added dropwise to a stirred mixture of p-nitrophenol (38 g) and triethylamine (55 g) in methylene chloride (1 L). The mixture is stirred at RT for about 12 hours, refluxed for 3.5 hours, concentrated in vacuo, the residue is treated with saturated aqueous $Na_2CO_3$ solution, and the insoluble solid filtered and washed with water and $CH_2Cl_2$. This solid is recrystallized from ethyl acetate/acetonitrile yielding the p-nitrophenoxy compound as a crystalline solid, M.P.=220°-221° C.

Step 2. 3-Amino-5-methoxy-2-methyl-2H-1,2,4,6-thiatriazine-1,1-dioxide

Ammonia gas is bubbled into a stirred suspension of the p-nitrophenoxy compound from Step 1 above (11 g) in chloroform (150 ml) for 40 min. The reaction mixture is filtered and the solid residue is washed with chloroform and water. The solid is recrystallized from hot acetonitrile, filtered and dried in vacuo yielding the desired 3-Amino compound as a crystalline solid, M.P. =234°-235° C.

EXAMPLE 7

5-METHOXY-2-METHYL-3-[(3-(3-N,N-DIMETHYLAMINOMETHYL)PHENOXY)-PROPYLAMINO]-2H-1,2,4,6-THIATRIAZINE-1,1-DIOXIDE

A solution of 1-(dimethylaminomethyl)-3-(3-aminopropoxy)benzene (8.3 g) and triethylamine (4.5 g) in methylene chloride (10 ml) is added dropwise to a stirred suspension of 5-methoxy-2-methyl-3-p-nitrophenoxy-2H-1,2,4,6-thiatriazine-1,1-dioxide (12.6 g) in methylene chloride (100 ml) under nitrogen. The reaction mixture is stirred for about 1 hour, extracted with saturated aqueous $Na_2CO_3$, and the organic layer is dried over $MgSO_4$ and filtered. The filtrate is extracted with 3N HCl. The aqueous acidic extract is basified and extracted with methylene chloride. The organic extract is dried, filtered, and concentrated in vacuo to an oil which is chromatographed on a silica gel column (220 g) eluting with 5% MeOH in $CH_2Cl_2$. The major fractions are combined, concentrated and taken up in hot isopropanol, treated with charcoal, filtered and concentrated. The precipitate is filtered, dried, and recrystallized from hot isopropylacetate, yielding the desired product as a crystalline solid, M.P.=107-°109° C.

EXAMPLE 8

5-AMINO-3-[3-(3-N,N-DIMETHYLAMINOMETHYL)PHENOXY]PROPYLAMINO]-2-METHYL-2H-1,2,4,6-THIATRIAZINE-1,1-DIOXIDE

Liquid ammonia (10-15 ml) is added to a stirred solution of the phenoxypropylaminothiatriazine compound of Example 7 above (3.1 g) in methanol (60 ml) and cooled to dry ice/acetone bath temperatures in a bomb. The reaction mixture is heated to 75° C. for about 24 hours, cooled and concentrated in vacuo. The residue is taken up in $CH_2Cl_2$, dried over $Na_2SO_4$, filtered, concentrated, taken up in hot ethyl acetate, treated with charcoal, filtered and the filtrate concentrated and cooled resulting in the crystallization of the desired compound, M.P.=138-140° C.

EXAMPLE 9

5-METHOXY-2-METHYL-3-[3-(5-[1-(1-PIPERIDINYL)-1,2,3,4TETRAHYDRONAPHTHALOXY])PROPYLAMINO]-2H-1,2,4,6-THIATRIAZINE-1,1-DIOXIDE

A suspension of 5-methoxy-2-methyl-3-p-nitrophenoxy-2H-1,2,4,6-thiatriazine-1,1-dioxide (9.4 g) in methylene chloride is added to a stirred mixture of 1-(1-piperidinyl)-5-(3-aminopropoxy)-1,2,3,4-tetrahydronaphthalene (8.7 g) and triethylamine (4.0 g) methylene chloride (90 ml). The reaction mixture is stirred for about 12 hours at RT, extracted with saturated aqueous $Na_2CO_3$ and the methylene chloride layer dried over $MgSO_4$, filtered and concentrated in vacuo yielding the desired product as an oil.

EXAMPLE 10

5-AMINO-2-METHYL-3-[3-[5-[1-(1-PIPERIDINYL)1,2,3,4-TETRAHYDRONAPHTHALOXY]]propylamino]-2H-1,2,4,6-THIATRIAZINE-1,1-DIOXIDE Liquid ammonia (15–20 ml) is added to a stirred solution of the 5-methoxy-3-aminopropoxytetrahydronaphthalene compound of Example 9 above (13 g) in methanol (100 ml), cooled to dry ice/acetone bath temperatures in a bomb. The bomb is sealed and warmed to 90° C. and kept at 90° C. for about 70 hours. The reaction mixture is cooled to RT, and the insoluble solid is filtered, and washed with methanol and the filtrate evaporated. The solid is twice recrystallized from hot ethanol, and once from a mixture of hot 95% EtOH and methanol, yielding the desired product as a white crystalline solid, M.P. 242°–244° C.

EXAMPLE 11

3-[2-(([2-Guanidino]thiazol-4-ylmethylthio)ethyl)amino]-5-Methoxy-2-methyl-2H-1,2,4,6-thiatriazine-1,1-dioxide A suspension of 5-methoxy-2-methyl-3-p-nitrophenoxy-2H-1,2,4,6-thiatriazine-1,1-dioxide (9.4 g) in methylene chloride is added to a stirred mixture of 2-guanidino-4-(2-aminoethylthiomethyl)thiazole dihydrochloride (9.1 g) and triethylamine (13 g) in methylene chloride (100 ml) and stirring continued at RT overnight. The reaction mixture is partitioned between saturated aqueous Na2CO3 and chloroform/methylene chloride. The organic layer is dried, filtered and evaporated yielding the desired product as a foam.

EXAMPLE 12

5-Amino-3-[2-(([2-guanidino]thiazol-4-ylmethylthio)ethyl) Amino]-2-methyl-2H-l-,2,4,6-thiatriazine-1,1-dioxide hydrogen maleate Liquid ammonia ( 10 ml) is added to a solution of 3-[2-(([2-guanidino]thiazol-4-ylmethylthio)ethyl)amino]-5-methoxy-2-methyl-2H-1,2,4,6zine-1,1-dioxide (12.7 g) in methanol (70 ml) cooled to dry ice/acetone bath temperatures stirred in a bomb. The bomb is sealed and warmed to 90° C. and stirred for about 48 hours. The reaction mixture is cooled, excess ammonia evaporated and the mixture evaporated in vacuo. The foam residue is identified as the amino compound and is dissolved in acetone. A solution of maleic acid (3.4 g) in acetone is added to the solution of amino compound thereby forming a precipitate. The precipitate is filtered and taken up in hot methanol, treated with charcoal and filtered hot. The filtrate is cooled and the solid precipitate filtered and dried. The dried solid is taken up in absolute ethanol/methanol, treated with charcoal and filtered hot. The white precipitate is filtered and taken up in hot methanol, treated with charcoal, filtered and the crystalline precipitate filtered, washed with methanol and dried affording the desired maleate salt, M.P. 184–186° C.

EXAMPLE 13

3-Amino-2-Benzyl-5-Methoxy-2H-1,2,4,6-thiatriazine-1,1-dioxide

Step 1. Benzylsulfamic acid

Benzylisocyanate (13.3 g) is added dropwise to a stirred mixture of nitromethane (160 ml) and 15% fuming sulfuric acid (5.4 ml) at about 10° C. The reaction mixture is refluxed for about one hour, cooled to RT and the solid filtered and washed with nitromethene. The solid is suspended in ether, filtered and dried and used as a crude solid for the next step.

Step 2. Benzylsulfamoyl chloride

A stirred mixture of benzylsulfamic acid (73 g), PCl5 (81 g) in toluene (540 ml) is heated to 40–50° C. for one hour and refluxed for about 3 hours. The cooled mixture is filtered through Celite and the filtrate concentrated in vacuo to remove the toluene affording the desired product as a liquid.

Step 3. N-carbomethoxy-N'-benzylsulfamyl-O-methylisourea

A solution of benzylsulfamoyl chloride (168 g) in anhydrous THF (300 ml) is added dropwise to a stirred solution of N-carbomethoxy-O-methylisourea (107 g) and triethylamine (90 g) in anhydrous THF (800 ml) under nitrogen at −70° C. The resulting suspension is warmed to RT, filtered and the filtrate evaporated in vacuo. The residue is partitioned between methylene chloride and 0.5N aqueous HCl. The organic layer is dried, filtered, and concentrated in vacuo affording the desired product as an oil.

Step 4. 2-Benzyl-5-methoxy-2H-1,2,4,6-thiatriazin-3-one-1,1-dioxide

A solution of N-carbomethoxy-N'-benzylsulfamoyl-O-methylisourea (215 g) in anhydrous THF (200 ml) is added dropwise to a stirred suspension of sodium hydride (43 g of 60% dispersion) in anhydrous THF (900 ml) and refluxed for 2 hours under nitrogen. Water (800 ml) is added to the cooled reaction mixture and the aqueous mixture washed with ether. The pH of the aqueous layer is adjusted to about pH=3.2 and the resulting suspension extracted with methylene chloride. The methylene chloride extract is dried, filtered, and evaporated in vacuo. The residue is taken up in hot isopropyl alcohol, treated with charcoal, filtered hot, concentrated, cooled, the precipitate filtered and dried in vacuo yielding the desired product, M.P.=141°–144° C.

Step 5. 2-Benzyl-3-chloro-5-methoxy-2H-1,2,4,6-thiatriazine-1,1-dioxide

A stirred mixture of 2-benzyl-5-methoxy-2H-1,2,4,6-thiatriazine-3-one-1,1-dioxide (10.5 g) and PCl5 (12.2 g) in POCl3 (35 ml) is refluxed overnight. The reaction mixture is evaporated in vacuo at 50° C. affording the crude product as a oil.

Step 6. 2-Benzyl-5-methoxy-3-p-nitrophenoxy-2H-1,2,4,6-thiatriazine-1,1-dioxide

A solution of 2-benzyl-3-chloro-5-methoxy-2H-1,2,4,6-thiatriazine-1,1-dioxide (3.8 g) in methylene chloride (10 ml) is added dropwise to a stirred mixture of p-nitrophenol (1.7 g) and pyridine (2.4 g) in methylene chloride (20 ml). The reaction mixture is heated to reflux for 3 hours, cooled, washed with 3N aqueous HCl and saturated aqueous Na2CO3. The methylene chloride layer is dried over MgSO4, filtered and evaporated in vacuo yielding the desired product as an oil.

Step 7. 3-Amino-2-benzyl-5-methoxy-2H-1,2,4,6-thiatriazine-1,1-dioxide

Ammonia gas is bubbled into a stirred mixture of 2-benzyl-5-methoxy-3-p-nitrophenoxy-2H-1,2,4,6-thiatriazine-1,1-dioxide (11.7 g) in methylene chloride (110 ml) for about 40 min at RT. The reaction suspension is washed with saturated aqueous Na2CO3, the solid filtered, suspended in aqueous Na2CO3 and washed with water. The solid is taken up in hot acetonitrile, treated with charcoal and filtered hot. The solution is concentrated forming a precipitate which is filtered, washed with acetonitrile and dried, yielding the desired product as a solid, M.P.=249°-251° C.

EXAMPLE 14

5-Amino-2-benzyl-3-[3-[5-[1-(1-piperidinyl)-1,2,3,4-tetrahydronaphthaloxy]]propylamino]-2H-1,2,4,6-thiatriazine-1,1-dioxide Step 1. 2-Benzyl-5-methoxy-3-[3-[5-[1-(1-piperidinyl)-1,2,3,4-tetrahydronaphthyloxy]]-propylamino]-2H-1,2,4,6-thiatriazine-1,1-dioxide A solution of 2-benzyl-5-methoxy-3-p-nitrophenoxy-2H-1,2,4,6-thiatriazine-1,1-dioxide (7.8 g) and triethylamine (3.5 g) in methylene chloride (50 ml) is added to a stirred solution of 5-(3-aminopropoxy)-1-(1-piperidinyl)-1,2,3,4-tetrahydronaphthalene (10.5 g) in methylene chloride (75 ml) and the reaction mixture stirred at RT for about 16 hours. The reaction mixture is washed with saturated aqueous $Na_2CO_3$ and the organic layer dried with $MgSO_4$, filtered and the filtrate evaporated in vacuo. The residue is chromatographed on silica gel (36 g) eluting with ethyl acetate. The major fractions are combined and evaporated yielding the desired product as an oil which is used in the next step.

Step 2. 5-Amino-2-benzyl-3-[3-[5-[1-(1-piperidinyl)-1,2,3,4-tetrahydronaphthyloxy]]propylamino]-2H-1,2,4,6-thiatriazine-1,1-dioxide Liquid ammonia (30 ml) is added to a bomb containing a stirred solution of the 2-benzyl-5-methoxy compound of Step 1 above (11.6 g) in methanol (150 ml) cooled to dry ice/acetone bath temperatures. The bomb is sealed and stirred at 75-80° C. for about 60 hours. The reaction mixture is evaporated and the residue taken up in hot isopropyl alcohol, treated with charcoal, filtered hot and the filtrate concentrated. The resulting precipitate is filtered and washed with isopropyl alcohol yielding the desired product, M.P.=179-180° C.

Compounds of Formula I above may be prepared according to the reaction sequences described above or by obvious variations thereof. Representative examples of additional compounds of Formula I include:

3-amino-5-methoxy-2-n-butyl-2H-1,2,4,6-thiatriazine-1,1-dioxide;
3-amino-5-methoxy-2-methyl-2H-1,2,4,6-thiatriazine-1,1-dioxide;
3-amino-2-benzyl-5-methoxy-2H-1,2,4,6-thiatriazine-1,1-dioxide;
2-benzyl-3-ethylamino-5-methoxy-2H-1,2,4,6-thiatriazine-1,1-dioxide;
2-benzyl-5-methoxy-3-methylamino-2H-1,2,4,6-thiatriazine-1,1-dioxide;
3-amino-5-ethoxy-2-n-butyl-2H-1,2,4,6-thiatriazine-1,1-dioxide;
3-amino-5-methoxy-2-methyl-2H-1,2,4,6-thiatriazine-1,1-dioxide;
3-amino-2-benzyl-5-methoxy-2H-1,2,4,6-thiatriazine-1,1-dioxide;
3-amino-5-amino-2-n-butyl-2H-1,2,4,6-thiatriazine-1,1-dioxide;
5-amino-3-benzylamino-2-n-butyl-1,2,4,6-thiatriazine-1,1-dioxide;
5-amino-2-n-butyl-3-phenethylamino-1,2,4,6-thiatriazine-1,1-dioxide.

Various tests in animals have been carried out to show the ability of the compounds of this invention to exhibit pharmacological responses that can be correlated with activity in humans. These tests involve such factors as the effect of the compounds of Formula I on gastric secretion and their $H_2$ antagonist, antiulcer and cytoprotective activity. It has been found that the compounds of this invention when tested in the above variety of situations show a marked activity.

One such test is the gastric secretion test. This test is carried out as follows: Shay rats are fasted for 4-8 hours, and water is given ad lib. The rats are selected at random and separated into groups of 10. The animals are treated intraduodenally (I.D.) with the test compounds or the vehicle immediately subsequent to the ligation of the stomach at the pyloric sphincter. The animals are sacrificed with chloroform at 4 hours post-drug administration, the stomach removed and its contents assayed for volume, pH and total acids.

A second gastric secretion test is carried out on the dog. This is outlined in the *Handbook of Physiology*, Section 6: Alimentary Canal, Volume II: Secretion. American Physiology Society, Washington, D.C., 1967.

It has been found that the compounds of this invention, when subjected to the above gastric secretion tests, display marked ability to decrease gastric volume and gastric acidity. These tests are known to correlate well with gastric activity in humans and are standard tests used to determine anti-secretory properties.

The compounds of Formula I have been found to be histamine $H_2$-receptor antagonists by the results obtained in the following $H_2$-antagonist tests.

A. Isolated Guinea Pig Atria

The $H_2$-receptor antagonist activity of the compounds of Formula I is measured by observing the beat rate response versus compound concentration in isolated guinea pig atria. A discussion of criteria to evaluate these dose-response curves may be found in, E.J. Ariens, G.A.J. vanOs, A.M. Simonis, and T.M. van Rossum, "A Molecular Approach to General Pharmacology", Sections 11A, 11B, and 111, *Molecular Pharmacology: The Mode of Action of Biologically Active Compound*. Vol. 1, Academic Press (1964).

1. Tissue Bath

A fifty ml jacketed tissue bath is maintained at 30° C. The bath consists of a Krebs-Henseleit buffer aerated with 95% $O_2$ - 5% $CO_2$, (pH 7.4). The buffer is prepared by mixing: 4 ml of an aqueous (distilled deionized) solution of $CaCl_2$. $2H_2O$ (0.37 g/ml); 4 ml of an aqueous (distilled deionized) solution of $MgSO_4$. $7H_2O$ (0.29 g/ml); 7.2 g of glucose; and, 2 liters of aqueous (distilled deionized) solution containing NaCl (28 g), $NaHCO_2$ (8.4 g), KCl (1.4 g) and $KH_2PO_4$ (0.6 g).

2. Preparation of Atria

Male albino guinea pigs (400-700 g, preferably 500-600 g) are killed by a blow to the back of the head and exsanguinated by cutting jugular veins and carotid arteries. The thoracic skin is opened from this neck cut and the rib cage exposed. Both sides of the rib cage and the diaphragm are cut and laid back, exposing the heart. The heart is removed by cutting through the vessels above and behind it while it is slightly elevated with forceps holding the ventricle tip. The heart is immediately placed in warm, aerated buffer and further dissected in a large petri dish of the same buffer. Since the pericardium is removed, it is possible to slip iris scissors between the atria and ventricles while holding the aorta and vessels with tweezers and cut off the atria. The atria are then dissected from any remaining tissue and vessels and suspended in the bath using small, curved taperpoint needles formed into hooks and tied to an S-shaped hook and the L-shaped lower support with 00 silk.

A Beckman Type 9308 Strain Gauge Coupler connects a Beckman cardiotachometer to a Grass FT03C strain gauge supported in a rack and pinion clamp. The upper hook of the strain gauge is placed in the edge of the left atrium and the lower hook in the tip of the right atrium. The lower support is clamped in a femur clamp and the upper hook is suspended from the strain gauge lug. The strain gauge is raised until the resting tension on the tissue is 1 gram. The tissue is allowed to stabilize for about one hour with several buffer washings and tension adjustments before the addition of the test compounds.

3. Test Procedure

A control dose-response curve using cumulative, approximately tripling doses is obtained in all three running from 0.1 to 30.0 µM histamine (0.1, 0.3, 1.0, 3.0, etc.) In order to minimize volume changes when adding drugs to the bath, small volumes of concentrated solutions are used. It is convenient to make up a 0.5 M solution and dilute it to give 50, 5 and 0.5 mM solutions.

Data recorded consists of the initial baseline rate and the stable plateau rate after each addition. Histamine is then washed out and the tissues are allowed to stabilize again near the initial baseline rate; this may take several rinses and 1 hr. The test compound is then added at the same cumulative doses and rates again recorded. If the compound behaves as an agonist and stimulates, then the dose is increased until the rate plateaus or the concentration is 1.0 mM. If, however, no agonistic activity is observed when the concentrations has reached 100 µM then its antagonistic activity is assessed by repeating the histamine curve without washing out the test compound. Reversibility of effect is assessed by attempting to wash out the test compound and/or histamine and repeat the histamine curve. Erratic or irregular beating or any other abnormal behavior at any time is noted. Calculations consist of the change in rate from base line and that change as a percentage of the maximum rate obtained in the initial control curve. The mean of those percentages ($\pm$SEM) is plotted as a function of agonist concentration (either histamine or test compound) to evaluate the type of response.

B. Lumen Perfused Rat Stomach—Effect on the Gastric Secretion

Male Sprague-Dawley rats weighing between 350 and 500 gm are housed individually according to standard animal husbandry procedures and are deprived of food twenty-four hours prior to testing. The rats are anesthetized by an intraperitoneal injection of 25% solution of urethane (0.5 to 0.7 ml/100 g of body weight). Once anesthetized, the trachea is exposed and cannulated with PE 100 tubing. The jugular vein is exposed and cannulated with PE 50 tubing bevelled at the tip. The abdomen is opened through a midline incision, and the esophagus is isolated excluding the vagus nerve. PE 190 tubing, with a flange on one end, is passed down the rat's mouth through the esophagus and into the stomach. The esophagus is tied off and the tubing checked to make sure that it is securely in the stomach. The duodenum is then identified and a small cut made about 1 cm below the pyloric sphincter. A piece of PE 320 tubing (flanged at one end) is inserted through the cut and into the stomach. It is secured firmly by tying a ligature around the pylorus. Using a 50 ml syringe, the stomach is flushed out with 0.4 mM NaOH through the esophageal tube until the perfusate emerging from the pyloric tube is clear. The animal is placed on a tilted table covered with a Gordon-Rupp water blanket Model 'K' to maintain the rat's body temperature at 30° C. The tube going into the esophagus is attached to a Sage Peristaltic Pump and 0.4 mN NaOH (pH 10.0) is perfused and collected in 30 ml beakers. The beakers are changed every 10 or 15 minutes and the pH of these samples are recorded. Once the pH has stabilized around 6.5-7.5, drugs that affect gastric secretion are given intravenously. The effectiveness of a compound is based on its ability to prevent a drop in pH initiated by a gastric stimulant, such as histamine. See, Ghosh, M.N. and Schild, H.O., *Brit. J. Pharmacol.*, 13: 54 (1958).

Compounds within the scope of Formula I have also been determined to exhibit anti-ulcer activity. The anti-ulcer properties of these compounds can be evaluated using an anti-ulcer assay in which aspirin or another nonsteroidal anti-inflammatory agent is used to induce gastric ulcers in the rat according to the following test procedure.

See, Corell, T., "Interaction of Salicylates and other Non-steroidal Anti-inflammatory Agents in Rats as Shown by Gastro-ulcerogenic and Anti-inflammatory Activities, and Plasma Concentrations", Acta. Pharmacology et. Toxicology, 45, 225–231 (1979).

Male Sprague-Dawley rats 140–170 g are housed according to standard animal husbandry procedures. The rats are fasted twenty-four hours prior to testing. On the test day, rats are divided into groups of 5 or 10, with one group serving as controls and receiving vehicle (for example, distilled water or a 0.1% Tween 80 solution). The test compounds, using logarithmic doses, are administered at a dose volume of 10 ml/kg. Thirty minutes post-drug, the rats are orally administered (10 ml/kg) aspirin or indomethacin suspended in 0.1% Tween 80 at a dose of 150.0 or 20.0 mg/kg, respectively. Four hours following indomethacin administration (five hours after aspirin administration) animals are sacrificed via cervical dislocation; their stomachs are removed, opened along the greater curvature, and gently rinsed and examined for lesions with a 10×magnifying glass; the following scale is employed:

| Grade | Description |
| --- | --- |
| 0 | No lesions |
| 1 | 5 lesions, all < 2 mm |
| 2 | 5 lesions, at least 1 > 2 mm |
| 3 | 5–10 lesions, all < 2 mm |
| 4 | 5–10 lesions, at least 1 > 2 mm |
| 5 | 10 lesions, all < 2 mm |
| 6 | 10 lesions, at least 1 > 2 mm |
| 7 | Perforation |

The average ulcer severity ($\pm$S.E.) for each group of animals is calculated. The percent inhibition for each test compound is calculated as follows:

$$\% \text{ inhibition} = \frac{\text{Mean value for control} - \text{Mean value for experimental}}{\text{Mean value for control}} \times 100$$

The compounds of Formula I have also been determined to exhibit cytoprotective activity.

The cytoprotective effectiveness of the compounds of Formula I is evaluated according to the following test procedure.

Male Sprague-Dawley rats 150-200 g are housed according to standard animal husbandry procedures. The rats are fasted twenty-four hours prior to testing. On the test day, rats are divided into groups of 6, with one group serving as controls and receiving vehicle (for example, distilled water or a 0.5% Methocel solution). The test compounds, using logarithmically spaced doses, are administered at a dose volume of 5 ml/kg. Ten minutes post-drug, the rats are orally administered 1 ml of absolute alcohol, 0.2 N NaOH (1 ml) or 0.6 N HCl (1 ml), regardless of body weight. One hour after administration animals are sacrificed by cervical dislocation, their stomachs are removed, opened along the greater curvature, rinsed under running tap water and examined for lesions with a 2×-10× magnifying glass.

The reduction of lesion count, lesion severity score and ulcer index as compared to similar measurements made in the controls was expressed as a percentage. Measurement of statistical significance of the results was done by standard methods.

The average ulcer severity (±S.E.) for each group of animals is calculated. The percent inhibition for each test compound is calculated as follows:

% inhibition =

$$\frac{\text{Mean value for control} - \text{Mean value for experimental}}{\text{Mean value for control}} \times 100$$

The results of the anti-secretory, anti-ulcer and cytoprotective assays, detailed above, establish the utility of the compounds of the present invention in the treatment of peptic ulcers in mammals, including humans. These compounds both aid in the healing of such ulcers and also prevent their formation.

The most preferred cytoprotective compounds are the 5-amino-3-[3-[5-[1-(1-piperidinyl)-1,2,3,4-tetrahydronaphthyloxy]]propylamino]-2H-1,2,4,6-thiatriazine-1,1-dioxide compounds wherein the 2-position is substituted by methyl, n-butyl and benzyl.

In particular, the compounds according to Formulae I and II are useful: in the treatment and prevention of hyperacidity and gastrointestinal ulceration; for decreasing gastrointestinal acid secretion in mammals; and for enhancing the gastrointestinal resistance to gastrointestinal irritants in humans and other mammals.

For all these purposes, the compounds of this invention can be normally administered orally or parenterally. Oral administration is preferred.

The compounds according to the invention, preferably in the form of a salt, may be formulated for administration in any convenient way, and the invention includes within its scope pharmaceutical compositions containing at least one compound according to the invention adapted for use in human or veterinary medicine. Such compositions may be formulated in a conventional manner using one or more pharmaceutically acceptable carriers or excipients. Such compositions may also contain if required other active ingredients, for example, $H_1$-antagonists, or known antacids such as aluminum hydroxide, magnesium hydroxide, magnesium trisilicate, aluminum glycinate, or calcium carbonate. Suitable carriers include diluents or fillers, sterile aqueous media and various non-toxic organic solvents. The compositions may be formulated in the form of tablets, capsules, lozenges, troches, hard candies, powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of active compound to carrier are determined by the solubility and chemical properties of the compounds, the particular mode of administration and standard pharmaceutical practice. For example, excipients such as lactose, sodium citrate, calcium carbonate and dicalcium phosphate and various disintegrants such as starch, alginic acid and certain complex silicates, together with lubricating agents such as magnesium stearate, sodium lauryl sulphate and talc, can be used in producing tablets. For a capsule form, lactose and high molecular weight polyethylene glycols are among the preferred pharmaceutically acceptable carriers. Where aqueous suspensions for oral use are formulated, the carrier can be emulsifying or suspending agents. Diluents such as ethanol, propylene glycol, glycerin and chloroform and their combinations can be employed as well as other materials.

For parenteral administration, solutions or suspensions of these compounds in sesame or peanut oil or aqueous propylene glycol solutions, as well as sterile aqueous solutions of the soluble pharmaceutically acceptable salts described herein can be employed. Solutions of the salts of these compounds are especially suited for intramuscular and subcutaneous injection purposes. The aqueous solutions, including those of the salts dissolved in pure distilled water, are also useful for intravenous injection purposes, provided that their pH is properly adjusted, suitably buffered, and made isotonic with sufficient saline or glucose.

The dosage regimen in carrying out the methods of this invention is that which insures maximum therapeutic response until improvement is obtained and thereafter the minimum effective level which gives relief. Thus, in general, the dosages are those that are therapeutically effective in the treatment of gastrointestinal disease conditions or symptoms, such as duodenal and peptic ulcer. In general, the dose can be between about 0.1 mg/kg and 100 mg/kg (preferably in the range of 1 to 20 mg/kg), bearing in mind, of course, that in selecting the appropriate dosage in any specific case, consideration must be given to the patient's weight, general health, age, and other factors which may influence response to the drug. The daily dose can range from 1 to 4 times a day.

We claim:

1. A method for the treatment of gastrointestinal hypersecretory or ulcerogenic disorders of a human or other mammal comprising administering thereto an effective antiulcerogenic amount of a 1,2,4,6-thiatriazine-1,1-dioxide compound substituted in the 2-, 4-or 6- positions by hydrogen, lower alkyl, heterocycloalkyl, cycloloweralkyl, phenylloweralkyl or substituted phenylloweralkyl, and in the 3-and/or the 5-position by $NR_3R_4$ wherein:

$R_3$ is H or lower alkyl;

$R_4$ is H, lower alkyl, phenyl, substituted phenyl, phenylloweralkyl, substituted phenylloweralkyl, phenoxyloweralkyl, substituted phenoxyloweralkyl, or $-(CH_2)_m-Z-(CH_2)_n-B$;

provided that R$_4$ is —(CH$_2$)$_m$—Z—(CH$_2$)$_n$—B in at least one of the 3- or 5- positions; and wherein:

m and n are 0, 1, 2, 3 or 4, provided m+n=0;

Z is oxygen or sulfur;

B is phenyl, toluyl, heteroaryl, alkyl heteroaryl or phenyl, toluyl, heteroaryl or alkyl heteroaryl substituted by amino, aminoloweralkyl, loweralkylamino, diloweralkylamino, loweralkylaminoloweralkyl, diloweralkylaminoloweralkyl or azaheterocyclyl;

and wherein:

substituted phenyl means phenyl substituted by loweralkyl, halo, carboxyl, amino, loweralkylamino, amido, hydroxyl, nitro, cyano or sulfonyl;

heteroaryl means furyl, pyridyl, thiazolyl or thienyl; and azaheterocyclyl means piperidinyl, pyrrolidinyl, morpholinyl, azepinyl, pyrrolyl, imidazolyl, pyrazolyl, and thiamorpholinyl;

or a pharmaceutically acceptable salt thereof.

2. A compound, effective in the treatment of gastrointestinal disorders in mammals, of the formula

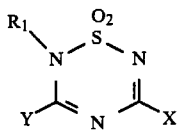

wherein:

R$_1$ is loweralkyl, heterocyclylalkyl, cycloloweralkyl, phenylloweralkyl or substituted phenylloweralkyl;

X and Y are each independently halo, hydroxy, loweralkyl, phenyl, substituted phenyl, loweralkoxy, mercaptyl, loweralkylmercaptyl, loweralkoxyloweralkyl, hydroxyloweralkyl, phenylloweralkyl, phenoxyloweralkyl, substituted phenylloweralkyl, substituted phenoxyloweralkyl, and NR$_3$R$_4$;

provided that at least one of X or Y is —NR$_3$R$_4$ and further provided that when X is —NR$_3$R$_4$, then Y is other than halo or hydroxy;

and wherein:

R$_3$ is H or loweralkyl;

R$_4$ is H, loweralkyl, phenyl, substituted phenyl, phenylloweralkyl, substituted phenylloweralkyl, phenoxyloweralkyl, substituted phenoxyloweralkyl, or —(CH$_2$)$_m$—Z—(CH$_2$)$_n$—B; 2)$_n$—B;

provided that at least one of X or Y is NR$_3$—(CH$_2$)$_m$—Z—(CH$_2$)$_n$—B;

m and n are 0, 1, 2, 3 or 4, provided m+n=0;

Z is oxygen or sulfur;

B is phenyl, toluyl, heteroaryl, alkyl heteroaryl or, phenyl toluyl, heteroaryl or alkyl heteroaryl substituted by amino, aminoloweralkyl, loweralkylamino, diloweralkylamino, loweralkylaminoloweralkyl, diloweralkylaminoloweralkyl or azaheterocyclyl;

and wherein:

substituted phenyl means phenyl substituted by loweralkyl, halo, carboxyl, amino, loweralkylamino; amido, hydroxyl, nitro, cyano or sulfonyl;

heteroaryl is furyl, pyridyl, thiazolyl or thienyl;

azaheterocyclyl is piperidinyl, pyrrolidinyl, morpholinyl, azepinyl, pyrrolyl, imidazolyl, pyrazolyl, or thaimorpholinyl, and heterocyclylalkyl means loweralkyl substituted by azaheterocyclyl;

or a pharmaceutically acceptable salt thereof.

3. A compound according to the formula

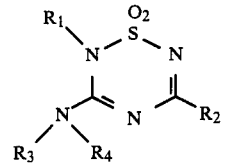

wherein:

R$_1$ is H, loweralkyl, heterocyclalkyl, cycloloweralkyl, phenylloweralkyl, substituted phenolloweralkyl;

R$_2$ is NR$_5$R$_6$, loweralkyl, phenyl, substituted phenyl, phenylloweralkyl, substituted phenylloweralkyl, loweralkoxy, phenoxy, substituted phenoxy, phenoxyloweralkyl, substituted phenoxyloweralkyl, hydroxyloweralkyl, loweralkoxyloweralkyl, halo, hydroxy, mercapto or loweralkylmercapto;

R$_3$ is H or loweralkyl;

R$_4$ is H, loweralkyl, phenyl, phenylloweralkyl, phenoxyloweralkyl, or substituted phenyl, substituted phenylloweralkyl, substituted phenoxyloweralkyl, or —(CH$_2$)$_m$—Z—(CH$_2$)$_n$—B;

R$_5$ and R$_6$ are each independently H, loweralkyl, phenyl, substituted phenyl, loweralkanoyl, carbamoyl, loweralkylcarbamoyl, —(CH$_2$)$_m$—Z—(CH$_2$)$_n$—B, or amidino;

provided that at least one of R$_4$, R$_5$ and R$_6$ is —(CH$_2$)$_m$—Z—(CH$_2$)$_n$—B;

and wherein:

Z is oxygen or sulfur;

m and n are 0, 1, 2, 3 or 4, provided m+n≠0; and

B is a phenyl, tolyl, furyl, pyridyl, thiazolyl, thienyl, naphthyl, indanyl, quinolinyl, isoquinolinyl, tetrahydronapthyl, tetrahydroquinolinyl, or tetrahydroisoquinolinyl group which may be substituted by loweralkyl amino, aminoloweralkyl, loweralkylamino, diloweralkylamino, loweralkylaminoloweralkyl, diloweralkylaminoloweralkyl, or azaheterocyclyl;

substituted phenyl means phenyl substituted by loweralkyl, halo carboxyl, amino, loweralkylamino, amido, hydroxyl, nitro, cyano or sulfonyl;

azaheterocyclyl means piperidinyl, pyrrolidinyl, morpholinyl, azepinyl, pyrrolyl, imidazolyl, pyrazolyl or thiamorpholinyl; and heterocyclylalkyl means loweralkyl sustituted by azaheterocyclyl;

or a pharmaceutically acceptable salt thereof.

4. A compound according to claim 3 wherein:

R$_1$ is H, loweralkyl, phenylloweralkyl or substituted phenylloweralkyl;

R$_2$ is amino, loweralkylamino, diloweralkylamino, or loweralkoxy;

R$_3$ is hydrogen; and

R$_4$ is —(CH$_2$)$_m$—Z—(CH$_2$)$_n$—B;

or a pharmaceutically acceptable salt thereof.

5. A compound according to claim 4 wherein:

B is

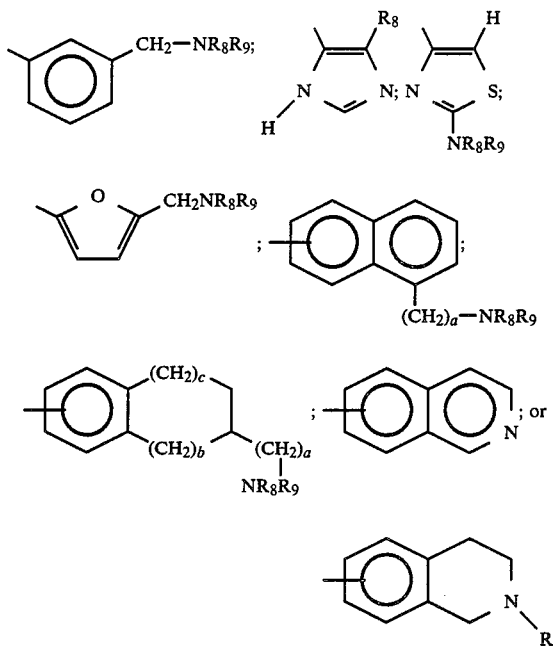

a is 0, 1 or 2;
b is 0 or 1;
c is 0, 1, 2 or 3;
R is H, lower alkyl, phenylloweralkyl or substituted phenylloweralkyl;
R$_8$ and R$_9$ are each independently H, loweralkyl, or amidino; or
R$_8$ and R$_9$ together are loweralkene and together with the nitrogen atom to which they are attached form a heterocycle which includes about two to about six carbon atoms and which may include one additional heteroatom of N, O or S; or a pharmaceutically acceptable salt thereof.

6. A compound according to claim 3, wherein:
R$_1$ is H, loweralkyl or phenylloweralkyl;
R$_2$ is NH$_2$;
R$_3$ is H or loweralkyl; and
R$_4$ is a bicyclic benzenoid alkylene ether group of the formula

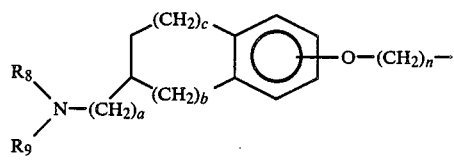

wherein:
a, b and c are 0, 1 or 2;
n is 2, 3 or 4;
R$_8$ and R$_9$ are each independently H or loweralkyl; or
R$_8$ and R$_9$ together with the nitrogen to which they are attached form a hetero ring of either the formula

where Y is alkylene of one to six carbon atoms, or morpholinyl, azepinyl, pyrrolyl, imidazolyl, pyrazolyl or thiamorpholinyl;
or a pharmaceutically acceptable salt thereof.

7. A compound according to claim 6 wherein:
a is 0 or 1;
b is 0;
c is 1 or 2;
n is 3 or 4;
R$_1$ is lower alkyl;
R$_3$ is H; and
NR$_8$R$_9$ is 1-piperidinyl, 1-pyrrolidinyl or 1-morpholinyl; or
a pharmaceutically acceptable salt thereof.

8. A compound according to claim 6 which is 5-amino-2-n-butyl-3-[3-[5-[[1-(1-piperidinyl)]-1,2,3,4-tetahydronaphthaloxy]]propylamino]-2H-1,2,4,6-thiatriazine-1,1-dioxide or a pharmaceutically acceptable salt thereof.

9. A compound according to claim 6 which is 5-amino-2-methyl-3-[3-[5-[[1-(1-piperidinyl)]-1,2,3,4-tetrahydronaphthaloxy]]-propylamino]-2H-1,2,4,6-thiatriazine-1,1-dioxide or a pharmaceutically acceptable salt thereof.

10. A compound according to claim 6 which is 5-amino-2-benzyl-3-[3-[5-[[1-(1-piperidinyl)]-1,2,3,4-tetrahydronaphthaloxy]]-propylamino]-2H-1,2,4,6-thiatriazine-1,1-dioxide or a pharmaceutically acceptable salt thereof.

11. A compound according to claim 5, which is 3-[3-[3-(N,N-Dimethylaminomethyl)phenoxy]-propylamino]-6-methyl-6H-1,2,4,6-thiatriazin-5-one-1,1-dioxide or a pharmaceutically acceptable salt thereof.

12. A compound according to claim 5, which is 3-amino-6$^2$methyl-5-[3-[3-(1-piperidinylmethyl)phenoxy]-propylamino]-6H-1,2,4,6-thiatriazine-1,1-dioxide or a pharmaceutically acceptable salt thereof.

13. A compound according to claim 5, which is 5-amino-2-methyl-3-[(3-(3-N,N-dimethylaminomethyl)-phenoxy)propyl amino]-2H-1,2,4,6-thiatriazine-1,1-dioxide or a pharmaceutically acceptable salt thereof.

14. A compound according to claim 5, which is 5-amino-2-methyl-3-[(5'-methyl-4'-imidazoyl)methylthio-ethylamino]-2H-1,2,4,6-thiatriazine-1,1-dioxide or a pharmaceutically acceptable salt thereof.

15. A compound according to claim 5, which is 5-amino-2-n-butyl-3-[(3-(3-N,N-dimethylaminomethyl)-phenoxy)-propylamino]-2H-1,2,4,6-thiatriazine-1,1-dioxide or a pharmaceutically acceptable salt thereof.

16. A compound according to claim 5, which is 5-amino-2-n-butyl-3-[(2-(2-guanidino)thiazol-4-yl methythio)ethyl]amino-2H-1,2,4,6-thiatriazine-1,1-dioxide or a pharmaceutically acceptable salt thereof.

17. A compound according to claim 5, which is 5-amino-3-[2-(5-N,N-dimethylaminomethyl-2-furanylmethylthio)ethylamino]2-methyl-2H-1,2,4,6-thiatriazine-1,1-dioxide or a pharmaceutically acceptable salt thereof.

18. A compound according to claim 5, which is 5-amino-3-[(2-(2-guanidino)thiazol-4-ylmethylthio)ethylamino-2-methyl-2H-1,2,4,6-thiatriazine-1,1-dioxide or a pharmaceutically acceptable salt thereof.

19. A compound according to claim 5, which is 5-methoxy-2-methyl-3-[(3-N,N-dimethylaminomethyl)-phenoxy)propylamino]-2H-1,2,4,6-thiatriazine-1,1-dioxide or a pharmaceuticaly acceptable salt thereof.

* * * * *